United States Patent [19]
Menzin et al.

[11] Patent Number: 6,102,924
[45] Date of Patent: Aug. 15, 2000

[54] SCALPEL ESPECIALLY FOR CESAREAN SECTIONS AND METHOD OF ITS USE

[76] Inventors: Andrew W. Menzin, 127 Andover Rd., Roslyn Heights, N.Y. 11577; Myles S. Kobren, 100 Manetto Hill Rd.-Ste 302, Plainview, N.Y. 11803

[21] Appl. No.: 09/375,757

[22] Filed: Aug. 18, 1999

[51] Int. Cl.⁷ .................................................. A61B 17/32
[52] U.S. Cl. ................................. 606/167; 30/2; 30/151; 30/335
[58] Field of Search ..................... 606/119, 159, 606/167, 182, 185; 30/2, 151, 158, 167, 335, 339

[56] References Cited

U.S. PATENT DOCUMENTS

| | | | |
|---|---|---|---|
| 4,960,419 | 10/1990 | Rosenberg | 606/167 |
| 5,309,641 | 5/1994 | Wonderley et al. | 30/151 |
| 5,312,429 | 5/1994 | Noack | 606/167 |
| 5,481,804 | 1/1996 | Platts | 30/162 |
| 5,662,669 | 9/1997 | Abidin et al. | 606/167 |
| 5,730,751 | 3/1998 | Dillon et al. | 606/167 |
| 5,908,432 | 6/1999 | Pan | 606/167 |
| 5,919,201 | 7/1999 | Carter et al. | 606/167 |
| 5,938,676 | 8/1999 | Cohn et al. | 606/167 |
| 5,941,892 | 8/1999 | Cohn et al. | 606/167 |

*Primary Examiner*—Gene Mancene
*Assistant Examiner*—Pedro Philogene
*Attorney, Agent, or Firm*—Eliort S. Gerber

[57] ABSTRACT

In performing cesarean section (c/section) surgery, and other surgery, a scalpel blade is used having a blunt and rounded edge to divide or separate tissue. In a cesarean section a scalpel with a sharp edge is first used to begin the uterine incision. A scalpel blade with a blunt and rounded edge is then used to continue the incision through the uterine wall to the amniotic cavity. The blunt edge scalpel blade reduces the possibility of lacerating the baby during delivery.

9 Claims, 3 Drawing Sheets

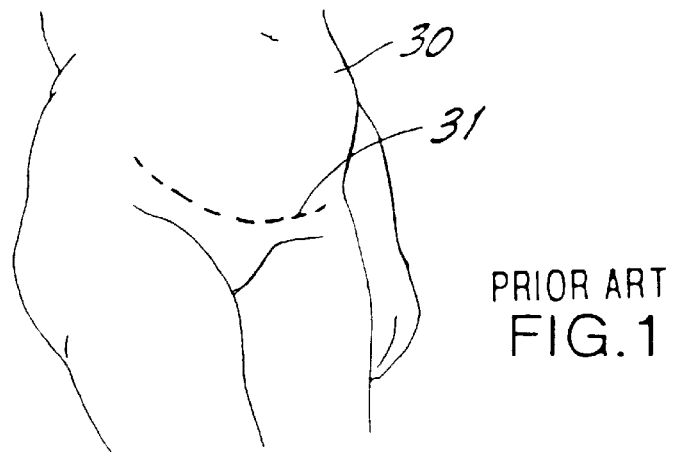
PRIOR ART
FIG.1
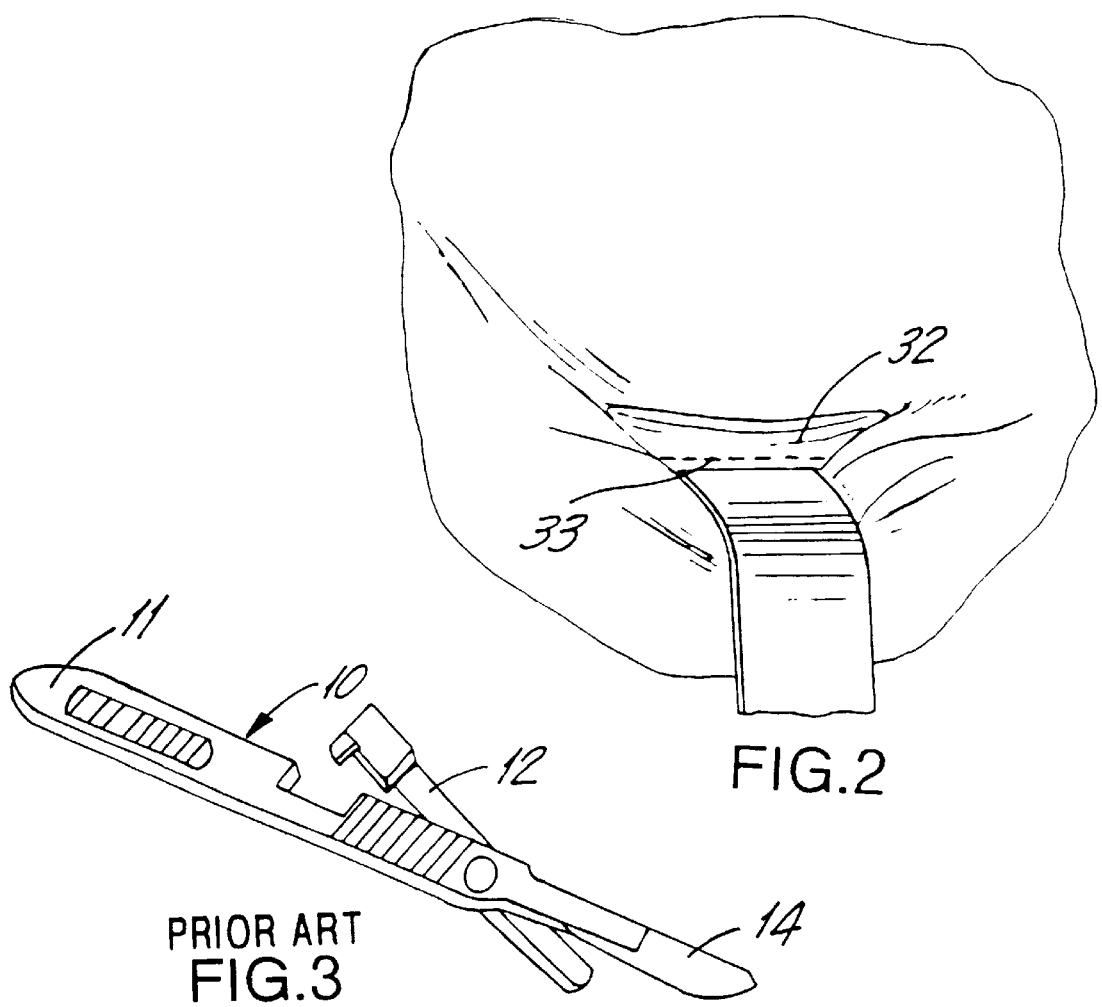
FIG.2
PRIOR ART
FIG.3

SCALPEL ESPECIALLY FOR CESAREAN SECTIONS AND METHOD OF ITS USE

FIELD OF THE INVENTION

The present invention relates to medical instruments and methods and more particularly to the scalpels, and methods, used in performing the surgical operation cesarean section and other surgical procedures.

BACKGROUND OF THE INVENTION

At the present time the cesarean section, commonly called "c/section", is one of the most widely used surgical procedures. According to the American College of Obstetrics and Gynecology, there were 799,033 cesarean sections performed in the United States in 1997. This represents approximately 25% of all deliveries; however, the specific rate of cesarean sections varies among hospitals and individual doctors.

A cesarean section is a major surgical procedure in which a baby is removed from the uterus by making a cut into the abdomen and then into the uterus. In many cases a cesarean section is necessary to save the life of the baby or the mother. In other cases a cesarean section is performed when a vaginal birth is not possible, e.g., failure of normal progression of labor. In some other cases a cesarean section may be scheduled due to a patient's request, or recommended by another doctor.

There are a number of potential complications that may occur as a result of a cesarean section. The complications include, but are not limited to, infection, bleeding, traumatic injury and death. It is estimated that the chance of dying from a cesarean section, which is a major abdominal surgery, is about 0.02% (20 out of 100,000), which is higher than the chance of dying from vaginal delivery. The reason cesarean sections may involve so many complications is because they involve opening up the abdomen and making an incision into the uterus. When doing a cesarean section an obstetrician/gynecologist (ob/gyn) doctor first makes sure that the patient has adequate anesthesia. They commonly use epidural or spinal anesthesia. On unusual occasions the patient may need to have general anesthesia, which involves putting the patient completely to sleep with a tube in the throat and the use of a ventilator device. Once the patient is anesthetized, a transverse incision about the size of the distance from the wrist to the tip of the ring finger is made into the skin, using a sharp scalpel. In most cases this incision is made from side-to-side, just above the pubic hair line (sometimes called a "bikini cut"). In other countries, and in some emergency situations, an up-and-down cut is made below the belly button to the top of the bikini line. Most doctors prefer bikini cuts because they heal and look better, and cause less pain after leaving the hospital. After cutting through the skin and underlying fat cells, the doctor will make a transverse incision, using a sharp scalpel, through the remaining tissue and then will enter the abdominal cavity. The bladder, uterus, ovaries, tubes and intestines are all visible. The vesicouterine fold is opened and the bladder is retracted. The uterus is then cut. When the uterus is cut the amniotic fluid will flow out, although in some cases there is only a small amount. Some doctors will then enlarge the cut in the uterus using their fingers. An alternative for lengthening the incision is to use a special scissor. After entering the uterus through the cut, the baby is carefully grasped, and the surgical assistant pushes on the top of the uterus to deliver the baby through the hole in the uterus.

Cesarean sections are a major surgery and can have many complications. Some complications that can occur, during or after a cesarean section, include heavy bleeding which may require blood transfusions, damage to the bladder or intestines, damage to blood vessels, infections of the uterus, kidneys, lungs or other areas, opening up of the skin incision, blood clots around the uterus or in the leg veins or lungs, and an inability of the blood to clot. On rare occasions, a hysterectomy may be performed to save the mother's life.

One of the most troubling adverse risks of cesarean sections is the possibility of cutting or nicking the baby while it is in the uterus, causing it to bleed. In some cesarean sections, and at some times, there is very little amniotic fluid to protect the baby. The baby, due to its position, may have a part of its body directly in contact with the inner wall of the uterus at the position where the doctor makes the incision through the uterus. The sharp scalpel may cut or nick the baby, causing an accidental laceration (cut). The baby's laceration, which is unexpected, may lead to extensive scarring and disfigurement. Such scarring and disfigurement may cause permanent or long-term damage, for example, amputation of a finger. Laceration of the nose, eyes, mouth or internal organs may be difficult or impossible to repair.

The cesarean section begins with an incision or cut on the skin. This cut is carried deeper until the abdomen is completely open (into the peritoneal cavity). The bladder, which is normally attached to the front of the uterus, is released. This is done by cutting the attachments of the bladder to the uterus and pushing it away. A cut is then made in the uterus. This cut is then carried deeper until the uterine wall is completely divided. The uterine incision is then extended by tearing the tissue or cutting it with a sharp scissor. The amniotic cavity, a baby sac with its surrounding fluid ("waters") is opened. The baby is then delivered and handed to the pediatric or baby care team. The after-birth, or placenta, is removed. The incision is closed and the abdominal wall is reapproximated.

Several points should be emphasized. The uterine wall can vary greatly in thickness, due to individual variation, prior surgery, the result of labor, and other factors. The amount of amniotic fluid present, that normally cushions the baby, can also vary markedly (even be depleted), especially following rupture of the membrane. These factors underscore the difficulty in creating the incision and may predispose a cesarean section to complications, involving both the mother and the baby.

SUMMARY OF THE INVENTION

The present invention provides an improvement in the surgical technique of the cesarean section, or other surgery, using a special blunt-edge scalpel blade or knife. Although the description is primarily in terms of cesarean section, the blunt-edge instruments (blade and knife) may be used with other surgical procedures.

The inventive scalpel blade, contrary to present practice, has a blunt or rounded edge. Presently scalpels and knives have a razor sharp edge. If touched to the skin, they will cause a laceration. However, the inventive blunt scalpel blade or knife may safely be drawn along the skin without damage. The use of the blunt devices (blunt scalpel blade or blunt knife) prevents any injury to the baby. Even if a part of the baby's body is pressed against the inner wall of the uterus at the point of the incision, so that the blunt edge device touches the baby, the baby will not be lacerated. The devices are sufficiently blunt so that they cannot lacerate or cause injury to the baby, yet they can still separate muscle fibers of the uterus.

Although the blunt blade scalpel may be used in various surgical procedures, its use will be described in detail only in connection with an improved cesarean section surgical procedure.

The first portion of the cesarean section procedure of the present invention is conventional. First, the patient is partially, or fully, anesthetized. Then a transverse incision (cut) is made in the abdomen using a sharp scalpel. For example, the incision may be the so-called bikini cut. In all cases, the incision is through the wall of the abdomen. The vesicouterine fold is opened and the bladder is retracted. Up to this point the surgical operation has followed the conventional and well-established procedure for cesarean sections.

In accordance with the present invention, the conventional sharp scalpel blade is used to form a superficial cut of the thin and tough outer layer of uterus. Usually this superficial cut is less than 1 mm in depth and is a transverse cut at the position of, and the length of, the conventional transverse cut in the uterus. The blunt scalpel blade will then be used, along the line of the superficial cut, to separate the muscle fibers of the uterus completely down through the entire uterus wall.

The amniotic cavity will be entered and the baby delivered. The operation will be completed in the traditional manner.

BRIEF DESCRIPTION OF THE DRAWINGS

The following detailed description is the inventors' presently known best mode of practicing the invention. The detailed description should be taken in conjunction with the accompanying drawings, in which:

FIG. 1 is a perspective view of the transverse incision in the abdominal wall in a cesarean section;

FIG. 2 is a perspective view of the uterus;

FIG. 3 is a top plan view of a conventional prior art scalpel;

DETAILED DESCRIPTION

Figure 3A:
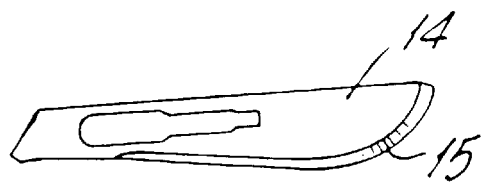
FIG. 3A is a top plan view of a prior art No. 22 scalpel blade.
Figure 3B:
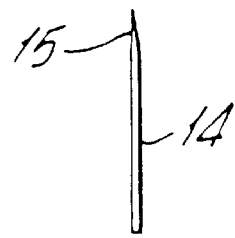
FIG. 3B is an enlarged end view of the sharp edge of the scalpel blade of FIG. 3A.

A typical prior art scalpel is shown in FIGS. 3–3B. It consists of a handle 10, of metal, which is sterilizable and reusable. One type of handle, the Saftylock (TM of Bard-Parker) has a main handle portion 11 and a pivotable portion 12 which pivots to lock the blade 14 on the handle. The scalpel blade 14 fits on the handle. The blade 14 is disposable and generally used only for a single operation, since it may become dull or nicked. The blade 14 has a razor-sharp edge 15. That edge is sufficiently sharp so that, with very little pressure, it will cut normal skin. For example, if lightly drawn across a finger, it will cut the skin and the finger will bleed. The blades have different shapes, called Numbers 10 through 25, and are available from Bard-Parker division of Becton-Dickinson, New Jersey. Generally the blades are available in stainless steel or carbon steel and may be individually wrapped to protect their sterility.

Figure 3C:
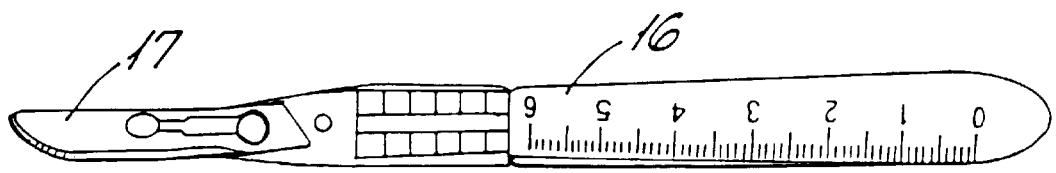
FIG. 3C is a top plan view of a prior art knife with a No. 10 scalpel blade.

A prior art disposable (single use) knife is shown in FIG. 3C. It consists of a plastic handle 16 which is fastened to a conventional sharp edge blade 17, a No. 10 blade being shown.

Figure 4A:
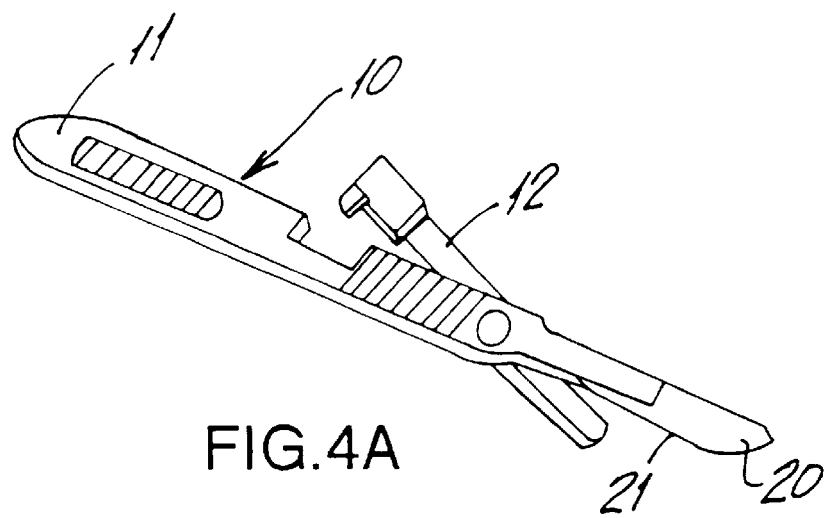
FIG. 4A is a perspective view of the blunt scalpel of the present invention.
Figure 4B:
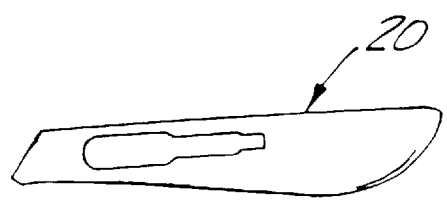
FIG. 4B is a top plan view of the blunt scalpel blade of FIG. 4A.
Figure 4C:
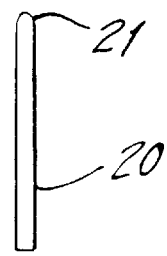
FIG. 4C is an enlarged end view of the blunt edge of the scalpel blade of FIG. 4B.
Figure 5A:
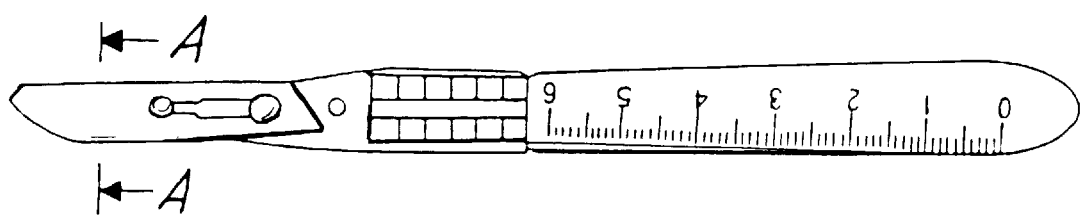
FIG. 5A is a top plan view of the blunt knife of the present invention.
Figure 5B:
FIG. 5B is a greatly enlarged cross-sectional view of the blunt blade of the knife of FIG. 5A taken along line A—A of FIG. 5A.

The scalpel of the present invention is shown in FIGS. 4A–4C. It uses the conventional metal non-disposable handle 10. However, its blade 20 has a blunt (unsharp) edge 21. The edge 21 is rounded, like that of a butter knife. The blade 20 does not have a sharp edge at any of its edges. If lightly, or strongly, drawn on normal skin, the blunt edge 21 will not cut or penetrate. It will not form an incision on normal skin. Preferably the blade 20 is 2 to 5 times thicker than a conventional blade.

It might be thought that, since the blunt edge 21 cannot cut skin, it could not be used in surgery to form an incision through a uterus wall, or in certain other surgical procedures to form an incision. However, the uterus wall, below the level of the thin tough outer skin layer, is not as tough or resilient as skin. It may be severed using a blunt edge. It is muscle fiber having the consistency and texture similar to that of uncooked chicken breast.

In the cesarean section procedure of the present invention, the patient 30, FIG. 1, is partially or fully anesthetized. A transverse incision (cut) 31 is made using a sharp scalpel. The incision is through the wall of the abdomen. Then the vesicouterine fold is opened and the bladder is retracted, as seen in FIG. 2. A sharp scalpel is then used to cut a shallow incision 33, preferably of less than 1 mm, through the tough outer surface layer of the uterus. That incision is transverse and of the length of the opening that will be formed.

The blunt scalpel blade 20 is then used to follow the entire length of the shallow incision line 33. It separates muscle fiber and opens up the uterus wall, forming a transverse incision (FIG. 2). That incision 32 is through the wall of the uterus, e.g., through the myometrium and the endometrium.

The remainder of the cesarean section operation is conventional. The incision 32 may, if desired, be enlarged by hand pressure. The baby is extracted and the uterus and abdomen repaired.

In addition to the possibility of accidental laceration of the baby, the use of a sharp scalpel also has the risk of the doctor extending the transverse incision too far and cutting blood vessels or muscle structure on the sides of the uterus. The use of the blunt scalpel of the present invention avoids that risk. Although it will separate the uterine fibers, it is too blunt to sever blood vessels or muscle structure.

Most importantly, the blunt scalpel blade can help prevent traumatic injury to the baby. The baby's body is, at times, directly flush with the inner wall of the uterus. During many cesarean sections the amniotic fluid cushion is absent. That cushion of fluid normally protects the baby from surgical trauma. Such trauma may ensue following the contact if a sharp blade scalpel should penetrate the uterine wall and accidentally come in contact with the baby's body surface, causing a laceration.

The article Smith, Hernandez & Wax, "Fetal Laceration at Cesarean Delivery" (Obs. & Gyn. Vol. 90, No. 3, September 1997, 344–346) found a rate of laceration of 1.9% in a review of 904 cesarean deliveries and concluded " . . . fetal laceration injury associated with cesarean delivery is not a rare event."

The present invention removes the potential hazard of the baby being lacerated during cesarean sections.

The term "scalpel blade", as used in the claims, includes the blade portion of a unitary one-piece disposable knife and the blades of two-piece scalpels having replaceable blades.

Modifications may be made in the present invention within the scope of the subjoined claims.

What is claimed is:

1. A scalpel adapted for medical surgery, having a blade with a blunt edge, which edge is sufficiently non-sharp so that the edge will not cut normal skin and the entire blade being without a sharp edge, said blade not being heated for thermal separation and not being connected to an electrical source for electrosurgery.

2. A scalpel as in claim 1 comprising a metal handle member adapted to be non-disposable and sterilizable and a blade which is disposable.

3. A scalpel as in claim 1 comprising a unitary disposable handle portion and blade.

4. A scalpel as in claim 1 wherein the blade has flat sides and the blunt edge is rounded when viewed in a cross-sectional view.

5. The method of performing a cesarean section to deliver a baby including the steps, in sequence, of:

(i) cutting an incision through the abdominal wall using a scalpel having a blade with a sharp edge which is sufficiently sharp to cut normal skin;

(ii) using a scalpel having a blade with a sharp edge to cut a shallow and elongated incision in the thin outer layer of the uterus at a depth of less than the thickness of the uterus;

(iii) using a scalpel having a blade with a blunt edge which is sufficiently non-sharp so that it will not cut normal skin to sever the uterus wall with the blunt edge, the severing being along the shallow incision formed in (ii), the blunt edge blade not having a sharp edge, and thereby forming an opening through which the baby may be delivered.

6. A method as in claim 5 wherein the incisions of (ii) and (iii) are transverse incisions.

7. The method of claim 5 wherein the scalpel comprises a metal handle member adapted to be non-disposable and sterilizable and a blade which is disposable.

8. The method of claim 5 wherein the scalpel comprises a unitary disposable handle portion and blade.

9. The method of claim 5 wherein the blade has flat sides and the blunt edge is rounded when viewed in an end view.

* * * * *